US011735307B2

United States Patent
Czaban et al.

(10) Patent No.: US 11,735,307 B2
(45) Date of Patent: Aug. 22, 2023

(54) INTERACTIVE LADDER

(71) Applicant: Conductive Education Center of Orlando, Inc., Winter Park, FL (US)

(72) Inventors: John T. Czaban, Winter Park, FL (US); Rob L. Catto, Orlando, FL (US)

(73) Assignee: CONDUCTIVE EDUCATION CENTER OF ORLANDO, INC., Winter Park, FL (US)

( * ) Notice: Subject to any disclaimer, the term of this patent is extended or adjusted under 35 U.S.C. 154(b) by 128 days.

(21) Appl. No.: 17/085,567

(22) Filed: Oct. 30, 2020

(65) Prior Publication Data

US 2021/0134424 A1 May 6, 2021

Related U.S. Application Data

(60) Provisional application No. 62/929,482, filed on Nov. 1, 2019.

(51) Int. Cl.
*G09B 19/24* (2006.01)
*G16H 20/30* (2018.01)

(52) U.S. Cl.
CPC ............. *G16H 20/30* (2018.01); *G09B 19/24* (2013.01)

(58) Field of Classification Search
CPC . G09B 19/24; A63B 2220/30; A63B 2220/40; A63B 2220/50
See application file for complete search history.

(56) References Cited

U.S. PATENT DOCUMENTS

2020/0222777 A1* 7/2020 Zimmerman ...... A63B 24/0003

* cited by examiner

*Primary Examiner* — Robert J Utama
(74) *Attorney, Agent, or Firm* — Greenberg Traurig, LLP; Mammen ("Roy") P. Zachariah

(57) ABSTRACT

An interactive ladder and method for using the interactive ladder are disclosed. The interactive ladder may include a plurality of rungs including sensors for detecting interactions made with the ladder. The interactive ladder may provide a signal indicating an activity to be selected and initiated via an application in communication with the interactive ladder. Upon detection of an interaction with the ladder and/or rung during the participation in the activity, a sensor may transmit a signal including an input associated with the interaction to a microcontroller for processing. The processed input may be provided to a computer to generate an output that includes feedback associated with the input associated with the interaction. The interactive ladder may cause the output including the feedback to be displayed on a display device of the interactive ladder, such as during participation of the activity provided by the program.

20 Claims, 7 Drawing Sheets

INTERACTIVE LADDER

CROSS-REFERENCE TO RELATED APPLICATIONS

This application claims the benefit of U.S. provisional application No. 62/929,482 filed on Nov. 1, 2020, the disclosure of which is hereby incorporated by reference in its entirety.

FIELD OF THE INVENTION

The present application relates to ladder technologies, interactive software technologies, educational learning technologies, gaming technologies, motor skill development technologies, and computing technologies, and more particularly, to an interactive ladder and an accompanying method for utilizing the interactive ladder.

BACKGROUND

In today's society, there exist a multitude of methodologies and systems for facilitating education and learning. For example, Conductive Education (CE) was developed many years ago to maximize the abilities of individuals with motor disabilities. The CE system has many unique elements and the equipment utilized in practice is just one of them. The specific tools utilized in CE were designed to maximize an individual's independence, while also learning everyday life skills. Once of the primary tools utilized in CE is the ladder/slider, which is a multifunctional equipment that can be utilized to improve and enhance the gross and fine motor skills of those with neurological disorders, such as cerebral palsy and other similar conditions. In addition, the ladder/slider is a device that enhances the educational process used in CE. Currently, the ladder/slider is mostly being used in the context of CE, however, therapy centers and rehabilitation facilities often utilize the ladder/slider during treatment as well.

Notably, the ladder/slider has had very little advancement since its creation and has never been integrated with technology. Although many types of therapy equipment and tools for individuals with cerebral palsy and other similar conditions have been improved upon, such equipment and tools still have deficiencies. With the growing presence of digital technology in everyday life, it is imperative that individuals with cerebral palsy and other similar disorders have equal opportunities and access to digital activities and games. While there have been numerous attempts at developing educational devices that would provide a fun, learning experience for individuals with cerebral palsy and similar disorders, such devices are typically not inclusive and are not accessible for everyone with such disorders. As a result, currently existing technologies are simply not engaging enough for individuals in today's society. Therefore, current technologies and processes may be modified and improved so as to provide enhanced functionality and features to enhance learning and increase participation in activities. Such enhancements and improvements may provide for improved user satisfaction, increased reliability, increased accuracy, increased efficiencies, increased access to meaningful data, substantially-improved activity participation rates, improved motor skills, improved contentment and happiness, and increased ease-of-use for users.

SUMMARY

An interactive ladder, a system including the interactive ladder, and methods for utilizing an interactive ladder are disclosed. In particular, the system and accompanying methods provide for an interactive ladder which may be utilized by users to develop motor skills, participate in activities, enhance learning, and perform a variety of tasks and/or functions, or a combination thereof. In particular, a goal of the interactive ladder is to automate and incentivize user interaction during the educational process, as well as enhance the user's motor skills. The digital adaptation provided by the interactive ladder allows for visual, audible, haptic, and/or other stimuli, intuitive feedback, and customization of therapeutic activities. In certain embodiments, the activities developed for the interactive ladder may be configured to mimic existing therapeutic activities, but may offer automated game-like or gamified digital versions of such activities. The digital aspects of the interactive ladder also enable the interactive ladder to conduct data collection and progress monitoring of such users.

Notably, in certain embodiments, the interactive ladder incorporates all the benefits of a standard ladder/slider, but also integrates microprocessor and simulation technology to create motivating tasks that users can receive feedback on as they are completing the tasks. Such additional incentive helps users to stay on task and ultimately complete a task. Additionally, the interactive ladder provides the ability to accurately detect human touch on specific surfaces of the interactive ladder, which also allows the interactive ladder to serve as a customized controller. For example, the interactive ladder can serve as a controller for an application that a user is interacting with while using the interactive ladder. The interactive ladder and its associated electronic components may be configured to send touch/release information to a computer, which may run software, developed in conjunction with therapists and subject matter experts.

In certain embodiments, the interactive ladder provides interaction capabilities to the traditional ladder chair utilized in CE. In certain embodiments, the interactive ladder may incorporate the use of a conductive component, such as conductive ink, on each rung of the interactive ladder, which may be utilized to divide each rung into two input sections. As a result, if the interactive ladder has six rungs, the interactive ladder may be configured to have twelve input sections, which may be configured to detect inputs into the interactive ladder and accompanying system. The interactive ladder may also incorporate the use of a microprocessor to decode the signals obtained via the input sections and may further incorporate a computer with a gaming engine to provide conductive education students with an interactive game (or other application) environment. In certain embodiments, the conductive component may be utilized to detect capacitive touches of the rungs of the interactive ladder (or other parts of the ladder in certain embodiments). Wires embedded in the frame of each rung of the interactive ladder may relay the touch/release data to a microprocessor (e.g. microcontroller), where the data may be processed and sent to an attached computer. The wiring and electronic components may be calibrated and the sensitivity may be tuned to prevent interference and false positive events. In certain embodiments, the conductive ink may be utilized to prevent alteration of the tactile response of the interactive ladder. Once the computer receives the data, the computer may further process the data and generate output data and/or feedback in response to the data and may present the output, such as on a display device of the interactive ladder.

Based on the foregoing, the interactive ladder brings CE into the realm of present-day and future technology. Users utilizing the interactive ladder may be able to receive feedback on the activities that they participate in and incentives on the activities that are designed to build their motor skills and concentration. Notably, the interactive ladder is accessible to users with severe motor difficulties and provides a platform to engage users in activities that can improve the quality of their motor skills. The interactive ladder captures the benefits of a traditional ladder, but also adds numerous digital benefits, such as, but not limited to, automation, data collection, and the potential for software updates to deliver new and customized therapeutic activities. These features enable the potential for users to work on their own or even at home. In addition to providing therapeutic activities for users, the interactive ladder also provides for activities that are just fun for the user and encourage creativity. For example, the interactive ladder may provide activities that allow the interactive ladder to be used as a musical instrument. As a result, the interactive ladder provides many benefits to users and further enhances and improves upon existing technologies.

To that end, in one embodiment according to the present disclosure, an interactive ladder is disclosed. The interactive ladder may include a display device, one or more rungs, one or more sensors configured to detect an interaction(s) with the rung(s). Additionally, the interactive ladder may include a microcontroller that may be configured to receive a signal containing an input associated with the interaction from the sensor. In certain embodiments, the signal containing the input may be provided by the sensor in response to the interaction with the rung being detected. The microcontroller may process the signal containing the input to determine additional information associated with the interaction conducted with the interactive ladder. The interactive ladder may further include a computer that may include a memory that stores instructions and a processor configured to execute the instructions to perform various operations. In certain embodiments, the computer may perform an operation that includes receiving the processed signal containing the input from the microcontroller, wherein the input provides information associated with the interaction with the rung. The computer may perform an operation that includes processing the processed input to generate an output including feedback associated with the input. Furthermore, the computer may perform an operation that includes causing the output including the feedback to be displayed on the display device in response to the input associated with the interaction.

In another embodiment, a method for utilizing an interactive ladder is disclosed. The method may include utilizing a memory that stores instructions, and a processor that executes the instructions to perform the various functions of the method. In certain embodiments, the memory and processor may be components of the interactive ladder itself and/or components of devices communicatively linked with the interactive ladder. In particular, the method may include detecting an interaction with a rung (or other part) of an interactive ladder. Additionally, the method may include transmitting, from a sensor that detected the interaction, a signal containing an input associated with the interaction with the rung (or other part) to a microcontroller for processing. The method may also include processing, by utilizing the microcontroller, the input to generate a processed input providing information associated with the interaction with the rung. The method may then include providing, to a processor of a computer communicatively coupled to the interactive ladder, the processed input for further processing. Furthermore, the method may include generating, based on the processing, an output including feedback associated with the input. Moreover, the method may include causing the output including the feedback to be displayed on a display device of the interactive ladder, wherein the output is displayed in response to the input associated with the interaction.

In a further embodiment, a system incorporating an interactive ladder is disclosed. The system may include an interactive ladder comprising any number of rungs, a sensor configured to detect an interaction with the rung(s) (or other part of the interactive ladder), and a microcontroller configured to receive, from the sensor, a signal containing an input associated with the interaction. In certain embodiments, the signal containing the input may be provided by the sensor in response to the interaction with the rung (or other part) being detected. The system may also include a computer including a memory and a processor configured to perform various operations of the system. The computer may perform an operation that includes receiving the signal containing the input from the microcontroller. In certain embodiments, the input may provide information associated with the interaction with the rung (or other part of the interactive ladder). Additionally, the computer may perform an operation that includes processing the input to generate an output including feedback associated with the input. Furthermore, the computer may perform an operation that includes causing the output including the feedback to be displayed or otherwise presented on a display device in response to the input associated with the interaction.

According to yet another embodiment, a computer-readable device having instructions for providing functionality for an interactive ladder is provided. The computer instructions, which when loaded and executed by a processor, may cause the processor to perform operations including: detecting an interaction with a rung of an interactive ladder; transmitting, from a sensor that detected the interaction, a signal containing an input associated with the interaction with the rung to a microcontroller for processing; processing, by utilizing the microcontroller, the input to generate a processed input providing information associated with the interaction with the rung; providing, to a processor, the processed input for further processing; generating, based on the processing, an output including feedback associated with the input; and causing the output including the feedback to be displayed on a display device of the interactive ladder, wherein the output is displayed in response to the input associated with the interaction.

These and other features of the interactive ladder, the systems incorporating the interactive ladder and methods for utilizing the interactive ladder are described in the following detailed description, drawings, and appended claims.

DETAILED DESCRIPTION OF THE INVENTION

Figure 1:
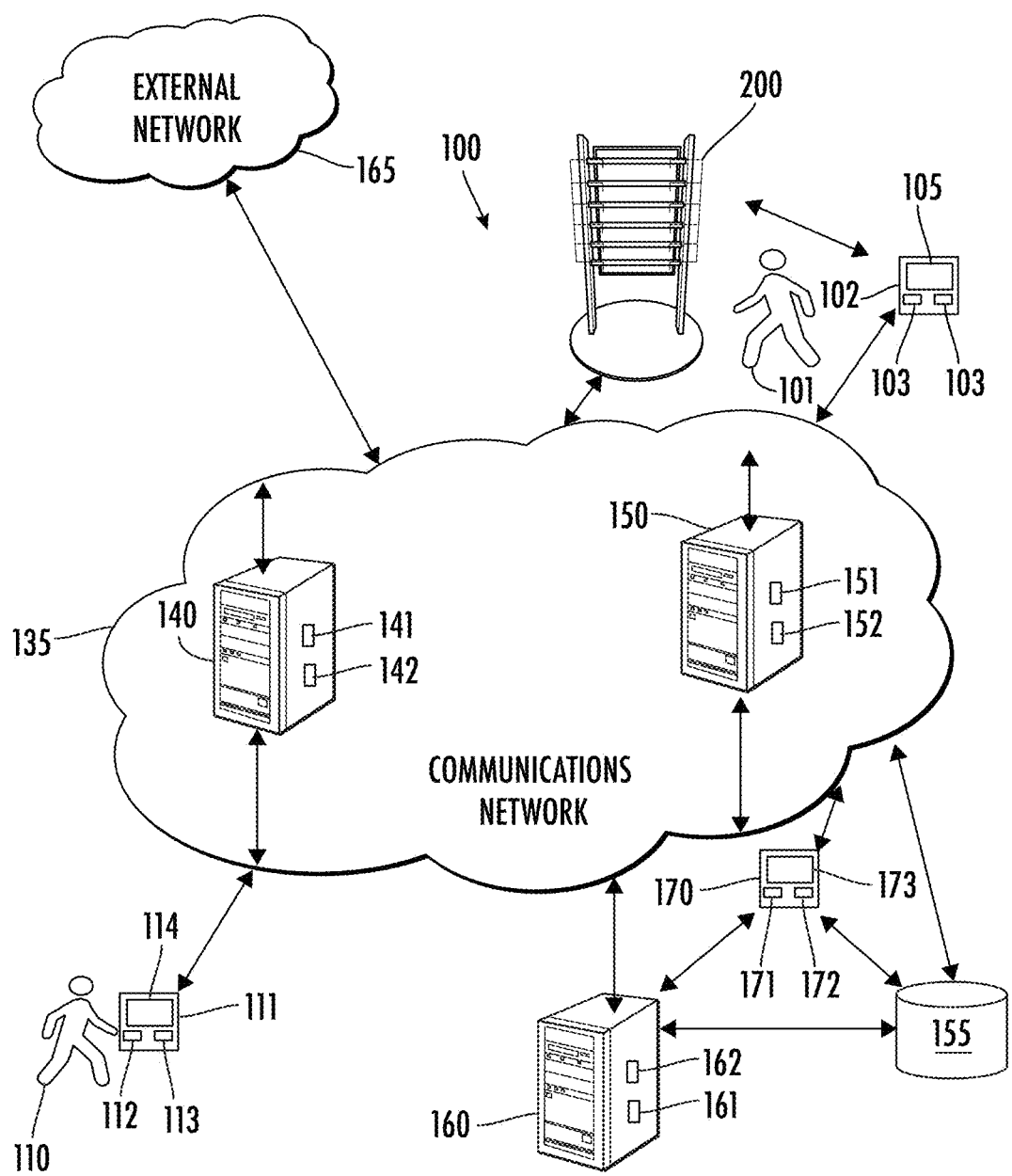
FIG. 1 is a schematic diagram of a system for providing and utilizing an interactive ladder according to an embodiment of the present disclosure.
Figure 2:
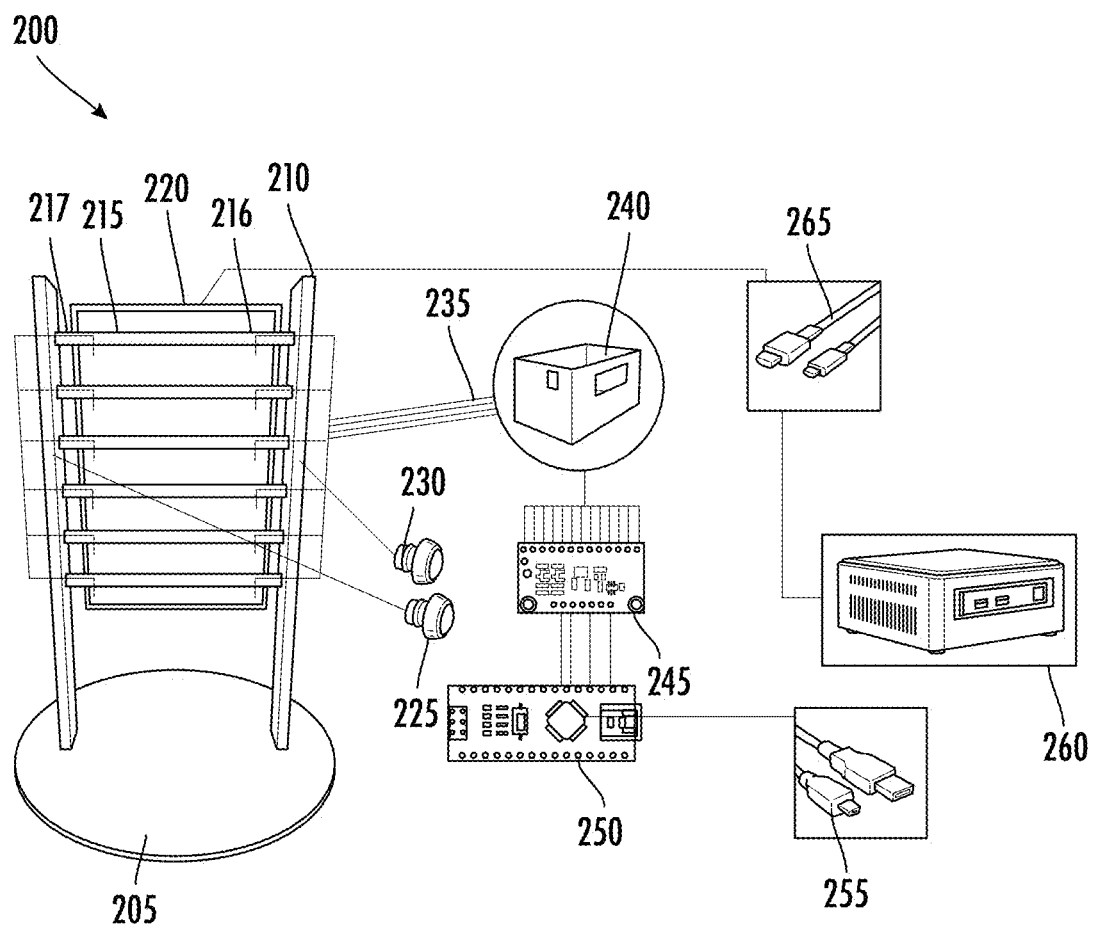
FIG. 2 is a diagram illustrating the interactive ladder of FIG. 1 and various components of the interactive ladder according to an embodiment of the present disclosure.
Figure 3:
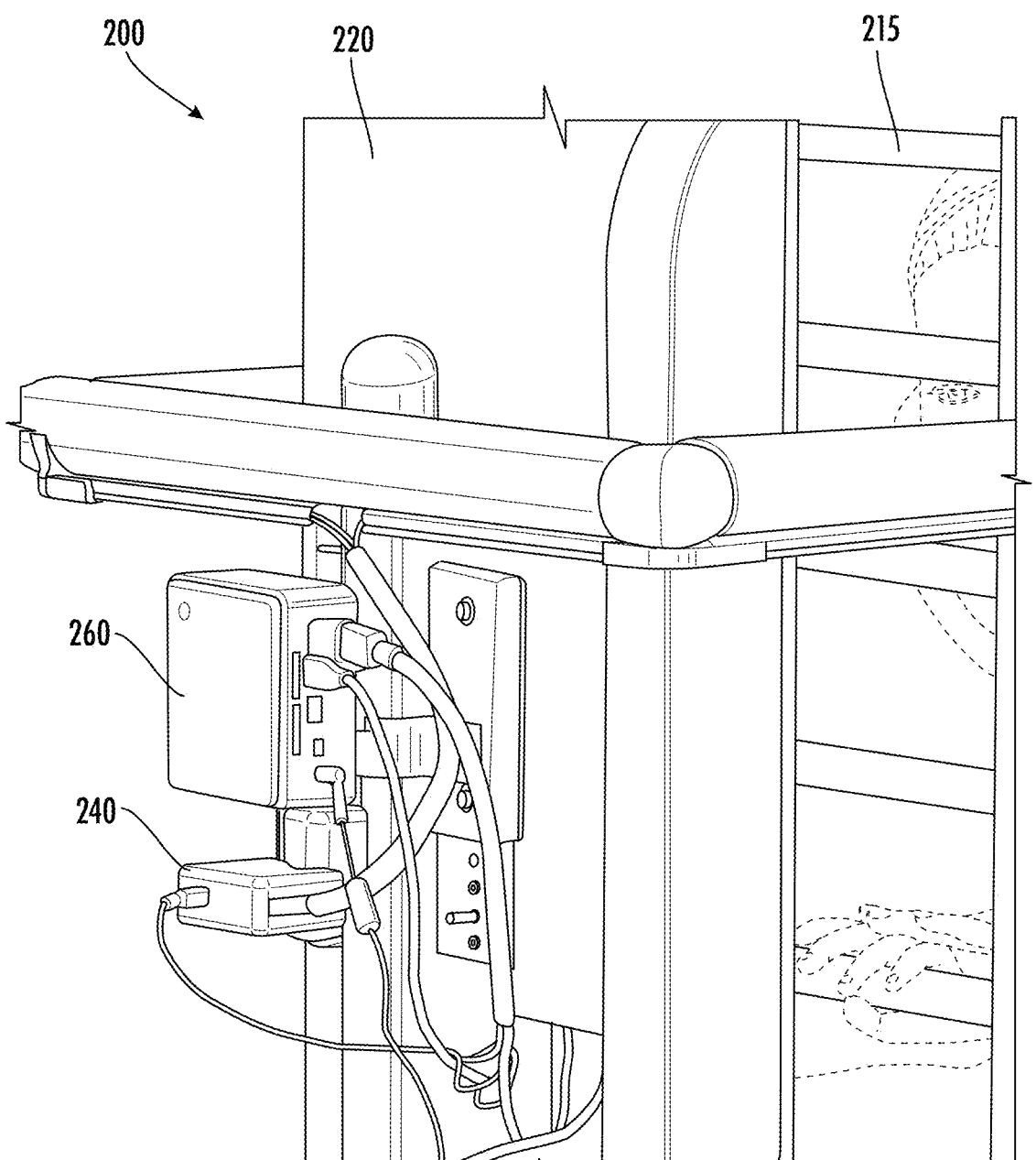
FIG. 3 is a back perspective view of the interactive ladder of FIG. 1, which features various components of the interactive ladder according to an embodiment of the present disclosure.
Figure 4:
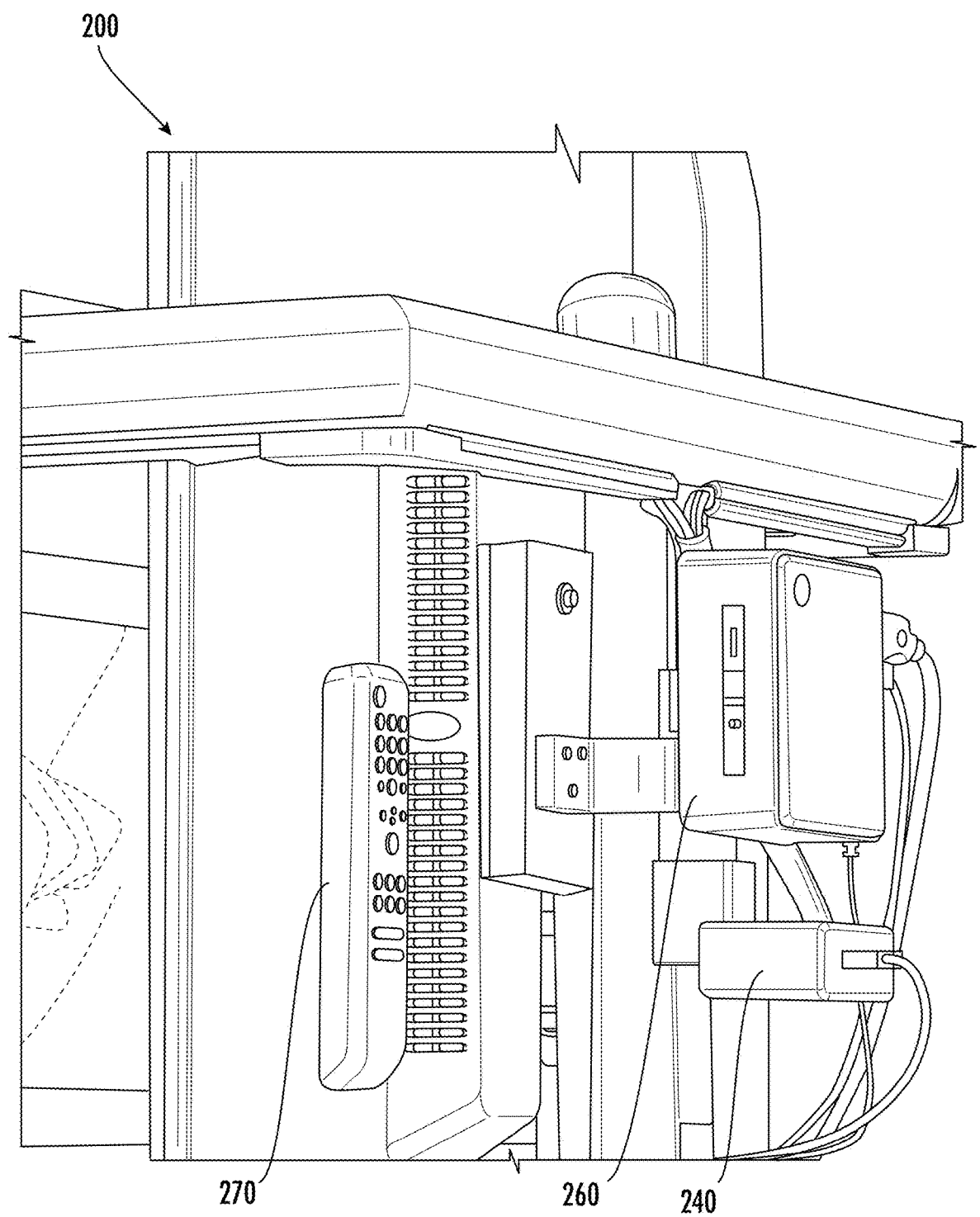
FIG. 4 is another back perspective view of the interactive ladder of FIG. 1, which features various components of the interactive ladder according to an embodiment of the present disclosure.
Figure 5:
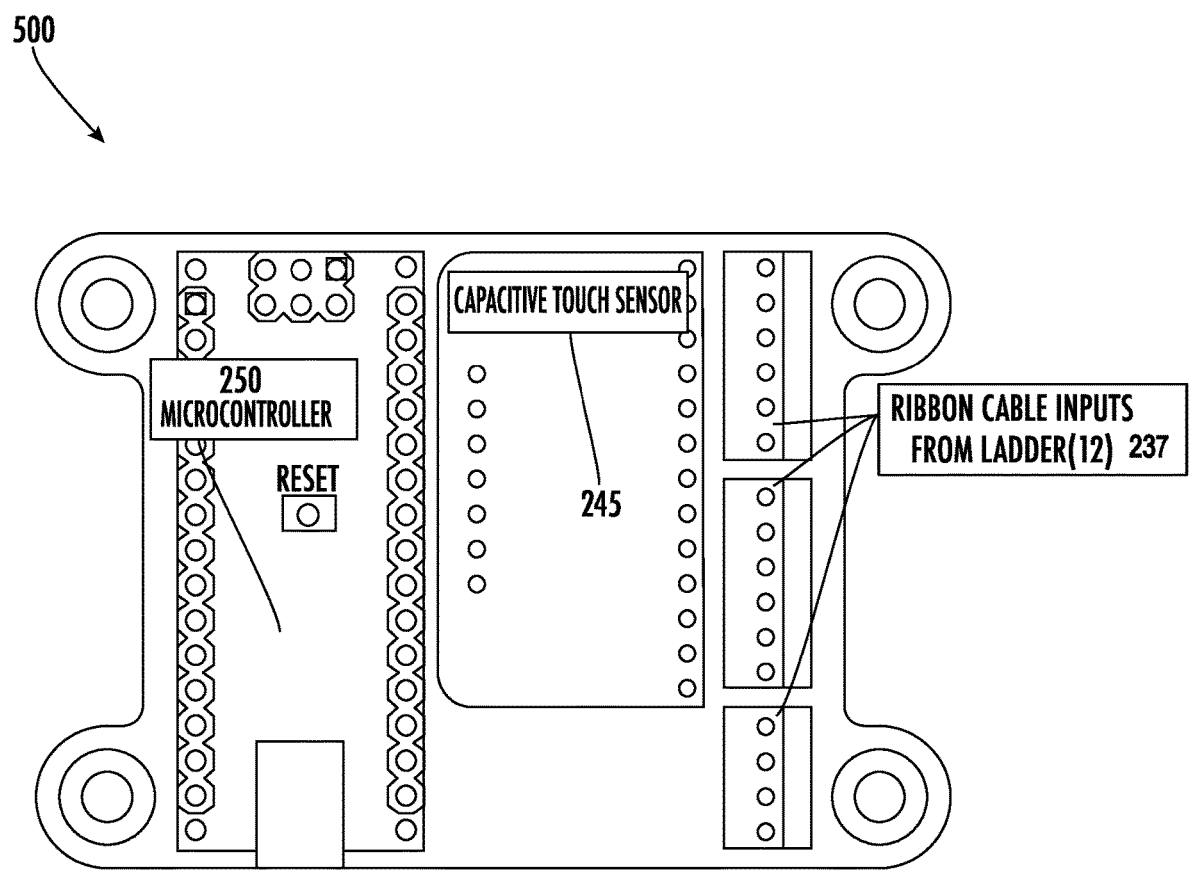
FIG. 5 is a diagram illustrating the microcontroller, the multi-channel sensor, and cable inputs for use with the interactive ladder of FIG. 1 according to an embodiment of the present disclosure.

An interactive ladder 200, a system 100 including the interactive ladder 200, and methods for utilizing an interactive ladder 200 are disclosed. In particular, the system 100 and accompanying methods provide for an interactive ladder 200 which may be utilized by users (e.g. first user 101 and second user 110) to develop motor skills, participate in activities, enhance learning, and perform a variety of tasks and/or functions, or a combination thereof. In particular, a goal of the interactive ladder 200 is to automate and incentivize user interaction during the educational process, as well as enhance the user's motor skills. The digital adaptation provided by the interactive ladder 200 allows for visual, audible, haptic, and/or other stimuli, intuitive feedback, and customization of therapeutic activities. In certain embodiments, the activities developed for the interactive ladder 200 may be configured to mimic existing therapeutic activities, but may offer automated game-like or gamified digital versions of such activities. The digital aspects of the interactive ladder 200 also enable the interactive ladder 200 to conduct data collection and progress monitoring of such users.

In particular, the interactive ladder 200 may include a plurality of rungs 215 including sensors 245 for detecting interactions made with the interactive ladder 200. In certain embodiments, the interactive ladder 200 may provide a signal indicating an activity to be selected and initiated via an application in communication with the interactive ladder 200. Upon detection of an interaction with the interactive ladder 200 and/or rung 215 during the participation in the activity, a sensor 245 may transmit a signal including an input associated with the interaction to a microcontroller 250 for processing. The processed input may be provided to a computer 260 to generate an output that includes feedback associated with the input associated with the interaction. The interactive ladder 200 may cause the output including the feedback to be displayed on a display device 200 of the interactive ladder 200, such as during participation of the activity provided by the program. In certain embodiments, other types of outputs may be provided as well. For example, audible outputs, haptic outputs, vibration outputs, virtual reality outputs, augmented reality outputs, text outputs, holographic outputs, any type of outputs, or a combination thereof, may be provided by the interactive ladder 200.

As shown in FIGS. 1-7, a system 100 and method for providing and using an interactive ladder 200 are disclosed. The system 100 may be configured to support, but is not limited to supporting, data and content services, data aggregation applications and services, simulation technologies, motor skill development technologies, educational technologies, gaming technologies, big data technologies, computing applications and services, cloud computing services, internet services, satellite services, telephone services, software as a service (SaaS) applications, mobile applications and services, and any other computing applications and services. The system may include a first user 101, who may utilize a first user device 102 to access data, content, and applications, or to perform a variety of other tasks and functions. As an example, the first user 101 may utilize first user device 102 to access an application (e.g. a browser or a mobile application) executing on the first user device 102 that may be utilized to access web pages, data, and content associated with the system 100. In certain embodiments, the first user 101 may be any type of user that may desire to improve their education, improve their motor skills, and/or may simply want to participate and have fun with an activity provided by an interactive ladder 200.

The first user device 102 utilized by the first user 101 may include a memory 103 that includes instructions, and a processor 104 that executes the instructions from the memory 103 to perform the various operations that are performed by the first user device 102. In certain embodiments, the processor 104 may be hardware, software, or a combination thereof. The first user device 102 may also include an interface 105 (e.g. screen, monitor, graphical user interface, audio device, neurotransmitter, etc.) that may enable the first user 101 to interact with various applications executing on the first user device 102, to interact with various applications executing within the system 100, and to interact with the system 100 itself. In certain embodiments, the first user device 102 may be a computer, a laptop, a tablet device, a phablet, a server, a mobile device, a smartphone, a smart watch, and/or any other type of computing device. Illustratively, the first user device 102 is shown as a mobile device in FIG. 1. The first user device 102 may also include a global positioning system (GPS), which may include a GPS receiver and any other necessary components for enabling GPS functionality, accelerometers, gyroscopes, sensors, and any other componentry suitable for a mobile device.

In addition to the first user 101, the system 100 may include a second user 110, who may utilize a second user device 111 to access data, content, and applications, or to perform a variety of other tasks and functions. As with the first user 101, the second user 110 may be a user that may desire to improve their education, improve their motor skills, and/or may simply want to participate and have fun with an activity provided by the interactive ladder 200. Much like the first user 101, the second user 110 may utilize second user device 111 to access an application (e.g. a browser or a mobile application) executing on the second user device 111 that may be utilized to access web pages, data, and content associated with the system 100. The second user device 111 may include a memory 112 that includes instructions, and a processor 113 that executes the instructions from the memory 112 to perform the various operations that are performed by the second user device 111. In certain embodiments, the processor 113 may be hardware, software, or a combination thereof. The second user device 111 may also include an interface 114 (e.g. a screen, a monitor, a graphical user interface, etc.) that may enable the second user 110 to interact with various applications executing on the second user device 111, to interact with various applications executing in the system 100, and to interact with the system 100. In certain embodiments, the second user device 111 may be a computer, a laptop, a tablet device, a phablet, a server, a mobile device, a smartphone, a smart watch, and/or any other type of computing device. Illustratively, the second user device 111 may be a computing device in FIG. 1. The second user device 111 may also include any of the componentry described for first user device 102.

In certain embodiments, the first user device 102 and the second user device 111 may have any number of software applications and/or application services stored and/or accessible thereon. For example, the first and second user devices 102, 111 may include education applications, applications for testing and/or improving motor skills, applications for analyzing and interpreting sensor data, artificial intelligence applications, machine learning applications, big data applications, applications for analyzing data, applications for synthesizing data, applications for integrating data, cloud-based applications, search engine applications, natural language processing applications, database applications, algorithmic applications, phone-based applications, product-ordering applications, business applications, e-commerce applications, media streaming applications, content-based applications, database applications, gaming applications, internet-based applications, browser applications, mobile applications, service-based applications, productivity applications, video applications, music applications, social media applications, presentation applications, any other type of applications, any types of application services, or a combination thereof. In certain embodiments, the software applications and services may include one or more graphical user interfaces so as to enable the first and second users 101, 110 to readily interact with the software applications.

The software applications and services may also be utilized by the first and second users 101, 110 to interact with any device in the system 100, any network in the system 100, or any combination thereof. For example, the software applications executing on the first and second user devices 102, 111 may be applications for receiving data, applications for storing data, applications for determining activities that the first and/or second users 101, 110 are suited for, applications for determining actions performed by the first and/or second users 101, 110, applications for receiving demographic and preference information, applications for transforming data, applications for executing mathematical algorithms, applications for generating and transmitting electronic messages, applications for generating and transmitting various types of content, any other type of applications, or a combination thereof. In certain embodiments, the first and second user devices 102, 111 may include associated telephone numbers, internet protocol addresses, device identities, or any other identifiers to uniquely identify the first and second user devices 102, 111 and/or the first and second users 101, 110. In certain embodiments, location information corresponding to the first and second user devices 102, 111 may be obtained based on the internet protocol addresses, by receiving a signal from the first and second user devices 102, 111, or based on profile information corresponding to the first and second user devices 102, 111.

The system 100 may also include a communications network 135. The communications network 135 of the system 100 may be configured to link each of the devices in the system 100 to one another. For example, the communications network 135 may be utilized by the first user device 102 to connect with other devices within or outside communications network 135. Additionally, the communications network 135 may be configured to transmit, generate, and receive any information and data traversing the system 100. In certain embodiments, the communications network 135 may include any number of servers, databases, or other componentry, and may be controlled by a service provider. The communications network 135 may also include and be connected to a cloud-computing network, a phone network, a wireless network, an Ethernet network, a satellite network, a broadband network, a cellular network, a private network, a cable network, the Internet, an internet protocol network, a content distribution network, any network, or any combination thereof. Illustratively, server 140 and server 150 are shown as being included within communications network 135.

Notably, the functionality of the system 100 may be supported and executed by using any combination of the servers 140, 150, and 160. The servers 140, and 150 may reside in communications network 135, however, in certain embodiments, the servers 140, 150 may reside outside communications network 135. The servers 140, and 150 may be utilized to perform the various operations and functions provided by the system 100, such as those requested by applications executing on the first and second user devices 102, 111. In certain embodiments, the server 140 may include a memory 141 that includes instructions, and a processor 142 that executes the instructions from the memory 141 to perform various operations that are performed by the server 140. The processor 142 may be hardware, software, or a combination thereof. Similarly, the server 150 may include a memory 151 that includes instructions, and a processor 152 that executes the instructions from the memory 151 to perform the various operations that are performed by the server 150. In certain embodiments, the servers 140, 150, and 160 may be network servers, routers, gateways, switches, media distribution hubs, signal transfer points, service control points, service switching points, firewalls, routers, edge devices, nodes, computers, mobile devices, or any other suitable computing device, or any combination thereof. In certain embodiments, the servers 140, 150 may be communicatively linked to the communications network 135, any network, any device in the system 100, or any combination thereof.

The database 155 of the system 100 may be utilized to store and relay information that traverses the system 100, cache information and/or content that traverses the system 100, store data about each of the devices in the system 100, and perform any other typical functions of a database. In certain embodiments, the database 155 may store the output from any operation performed by the system 100, operations performed and/or outputted by the interactive ladder 200, operations performed and/or outputted by any component, program, process, device, network of the system 100, or any combination thereof. For example, the database 155 may store data from sensors 245, data processed by the microcontroller 250, data processed by the computer 260, any other data, or a combination thereof. In certain embodiments, the database 155 may be connected to or reside within the communications network 135, any other network, or a combination thereof. In certain embodiments, the database 155 may serve as a central repository for any information associated with any of the devices and information associated with the system 100. Furthermore, the database 155 may include a processor and memory or be connected to a processor and memory to perform the various operations associated with the database 155. In certain embodiments, the database 155 may be connected to the servers 140, 150, 160, the first user device 102, the second user device 111, any devices in the system 100, any other device, any network, or any combination thereof.

The database 155 may also store information obtained from the system 100, store information associated with the first and second users 101, 110, store location information for the first and second user devices 102, 111 and/or first and second users 101, 110, store user profiles associated with the first and second users 101, 110, store device profiles associated with any device in the system 100, store communications traversing the system 100, store user preferences, store demographic information for the first and second users 101, 110, store information associated with any device or signal in the system 100, store information relating to usage of applications accessed by the first and second user devices 102, 111, store any information obtained from any of the networks in the system 100, store historical data associated with the first and second users 101, 110, store device characteristics, store information relating to any devices associated with the first and second users 101, 110, or any combination thereof. The database 155 may store algorithms for determining health disorders and/or conditions, algorithms for determining activities that the users are suited for, algorithms for determining abilities that the users have or can have, any other algorithms for performing any other calculations and/or operations in the system 100, or any combination thereof. In certain embodiments, the database 155 may be configured to store any information generated and/or processed by the system 100, store any of the information disclosed for any of the operations and functions disclosed for the system 100 herewith, store any information traversing the system 100, or any combination thereof. Furthermore, the database 155 may be configured to process queries sent to it by any device in the system 100.

The system 100 may also include a software application, which may be configured to perform and support the operative functions of the system 100 and/or the interactive ladder 200. In certain embodiments, the application may be a website, a mobile application, a software application, or a combination thereof, which may be made accessible to users utilizing one or more computing devices, such as first user device 102 and second user device 111. In certain embodiments, the application may not be connected to the internet networks may be configured to be executed via the computer 260 in a closed environment. In certain embodiments, the application of the system 100 may be accessible via an internet connection established with a browser program executing on the first or second user devices 102, 111, a mobile application executing on the first or second user devices 102, 111, or through other suitable means. Additionally, the application may allow users and computing devices to create accounts with the application and sign-in to the created accounts with authenticating username and password log-in combinations. The application may include a custom graphical user interface that the first user 101 or second user 110 may interact with by utilizing a web browser executing on the first user device 102 or second user device 111. In certain embodiments, the software application may execute directly as an installed program on the first and/or second user devices 102, 111, the computer 260, the servers 140, 150, 160, and/or the interactive ladder 200.

The software application may include multiple programs and/or functions that execute within the software application and/or are accessible by the software application. For example, the software application may include an application that generates web content, pages, and/or data that may be accessible to the first and/or second user devices 102, 111, the database 155, the external network 165, any type of program, any device and/or component of the system 100, or any combination thereof. The application that generates application content and pages may be configured to generate a graphical user interface and/or other types of interfaces for the software application that is accessible and viewable by the first and second users 101, 110 when the software application is loaded and executed on the interactive ladder 200, the computer 260, and/or the first and/or second computing devices 102, 111. The graphical user interface for the software application may display content associated with activities that users may participate in, gaming content, educational content, any type of content, or any combination thereof. Additionally, the graphical user interface may display functionality provided by the software application that enables the first and/or second user 101, 110 and/or the first user device and/or second user device 111 to interact with activities implemented by the software application, such as by utilizing the interactive ladder 200.

The system 100 may also include an external network 165. The external network 165 of the system 100 may be configured to link each of the devices in the system 100 to one another. For example, the external network 165 may be utilized by the first user device 102 to connect with other devices within or outside communications network 135. Additionally, the external network 165 may be configured to transmit, generate, and receive any information and data traversing the system 100. In certain embodiments, the external network 165 may include any number of servers, databases, or other componentry, and may be controlled by a service provider. The external network 165 may also include and be connected to a cloud-computing network, a phone network, a wireless network, an Ethernet network, a satellite network, a broadband network, a cellular network, a private network, a cable network, the Internet, an internet protocol network, a content distribution network, any network, or any combination thereof. In certain embodiments, the external network 165 may be outside the system 100 and may be configured to perform various functionality provided by the system 100, such as if the system 100 is overloaded and/or needs additional processing resources.

The system 100 may also include an interactive ladder 200, which may include a base 205, rails 210, rungs 215, conductive coatings 216, 217 that are applied to the rungs 215 of the interactive ladder and contact the wires of the cable 235, a display device 220, a button 225, a button 230, a cable 235 including wires that connect to input channels 237 of the circuit board 500 and to rungs 215 of the interactive ladder, an enclosure 240 (e.g. for housing sensor 245, microcontroller 250, and/or input channels 237), a sensor(s) 245, a microcontroller 250, a cable 255 for connecting the computer 260 to the microcontroller 250, a computer 260, a cable 265 to connect the computer 260 to the display device 200, a remote controller 270 for controlling the display device 220, speakers, haptic components, microphones, any type of input device, any type of output device, or any combination thereof. The interactive ladder 200 may be equipped with a collection of sensors, such as capacitive touch sensors and buttons. In certain embodiments, this allows the interactive ladder 200 to be utilized as an interactive controller, such as to control and interact with an application executing on the computer 260, without modifying the design of original equipment and therapeutic techniques. The interactive ladder 200 may include a microcontroller 250 and sensor(s) 245, which may be utilized to detect a user's interaction with the interactive ladder 200, such as with a rung 215 of the interactive ladder 200. For example, the sensor(s) 245, coatings 216, 217, and/or wires of the cable 235 may be tuned to detect human touch. The interactive ladder 200 may also include a computer 260, which may be utilized to execute the software application that can provide visual, audible, and/or other feedback through a display device 220 and/or other components of the interactive ladder 200, such as haptic components, speakers, and/or other output devices. The software application may be configured to present game-like versions of common physical therapy activities and challenges. Users, such as the first user 101, can select from a digital menu of activities. Each activity may provide its own instructions, objectives, and themes to create an enjoyable therapy session for users.

In certain embodiments, the interactive ladder 200 may be configured to record incoming data from the sensors 245, cables 235, and/or conductive coatings 216, 217 of the interactive ladder 200. For example, such data may be recorded using computer 260. Computer 260 may include a memory that stores instructions and a processor that executes the instructions to perform various operations, such as those supported by the interactive ladder 200. In certain embodiments, the computer 260 may be configured to analyze and visualize a user's performance with respect to participation in activities over time. In certain embodiments, the application executed by the computer 260 may generate activities that include cognitive challenges related to color, pattern matching, spelling, math, science, trivia, and/or any other subject of interest. In certain embodiments, activities may be generated with no objective, and, instead, may be utilized to encourage a user to play and have fun with the activity. For example, an activity may involve manipulating colors displayed on the display device 220 and/or playing musical notes through the speakers of the interactive ladder 220 by interacting with the rungs 215 of the interactive ladder 220. In certain embodiments, new activities and/or interactions may be generated to meet special and/or changing needs of users.

In certain embodiments, the interactive ladder 200 may include six rungs 215 with each rung 215 being divided into two input sections for receiving interactions/inputs from the users of the interactive ladder 200. In the six rung 215 embodiment, there may be twelve input sensors (2 on each rung 215) that are connected to and processed by the microcontroller 250, which may receive sensor data and signals from the sensor(s) 245 connected to the input sections. As interactions are detected by the sensor(s) 245, the microcontroller 250 may determine information about the sensor(s) 245 and/or buttons 225, 230, which may be utilized to select activities in the application and/or cancel and/or exit activities in the application. The microcontroller 250 may determine what is happening on the interactive ladder in terms of interactions and may provide this information to the computer 260. The computer 260 may receive the data and information from the microcontroller 250 and may determine and provide feedback and information about the user's interactions with the interactive ladder 200. In certain embodiments, the computer 260 may be configured to provide visual feedback on the display device 220 via cable 265. The computer 260 may also provide audible feedback via the cable 265 if the display device 220 has built-in speakers or an auxiliary 3.5 mm jack on the computer 260 for connecting external amplified speakers. The software application executing on computer 260 may be responsible for handling the context and specific aspects of the feedback. Each individual activity/exercise may be programmed to give feedback that is appropriate to a corresponding activity.

The display device 220 of the interactive ladder 220 may be configured to have its own power cord and/or power button to activate and/or deactivate the display device 200. The display device 220 may be connected to the computer 260 using the cable 265, which may be a HDMI Mini cable in certain embodiments. In certain embodiments, the computer 260 may utilize HDMI Mini and the display device 220 may utilize a standard HDMI port. In certain embodiments, the computer may be a mini computer and may be configured to include a mouse and keyboard. In certain embodiments, the display device 220 may be configured to be manually turned on or off. In certain embodiments, the computer 260 may have a power button that may act as a toggle for all systems associated with the interactive ladder 200, except for the display device 220. In certain embodiments, the computer's 260 power button may even toggle the display device 220 as well. In certain embodiments, if the computer 260 is powered off, the power button may start the computer 260 and launch the application associated with the interactive ladder 200. If the application is already running, the power button may be utilized to safely shutdown some or all systems and/or components of the interactive ladder 200. In certain embodiments, the computer may be set to automatically launch any necessary software upon startup. The software may also be manually launched by clicking on an icon for "CECO Play Center", for example.

Operatively, prior to using the interactive ladder 200, a user needs to ensure that the main power cable for the interactive ladder 200 is plugged in to an appropriate power outlet. The user may turn the computer 260 on and the display device 220. Each may have their own power buttons and indicator lights. The user may then wait for the computer to start up and the application software may then auto start, such as after a selected period of time (e.g. 60 seconds). A main menu of the application may load up and may be rendered on the display device 220. The user may then select one of a number of activities, such as by utilizing button 230. The user, such as first user 101, may then interact with the rungs 215 to navigate up and down on the activity menu. For example, if the user touches the bottom rung 215 that interaction may cause the program to navigate to the bottom of the menu. Similarly, as the user goes up the rungs 215, the program may gradually navigate up the menu options. If a user wants to exit or cancel a selected activity, the user may press the button 225, which may then return the user to the main menu.

In certain embodiments, the wiring of cable 235 may run throughout the interactive ladder 200 and may connect each ladder rung 215 to the microcontroller 250 and the sensor(s) 245. In certain embodiments, some wiring may be hidden in the construction of the interactive ladder 200, while plastic conduit may be utilized to conceal external wires that connect the sensor(s) 245. In certain embodiments, the conductive coatings 216, 217 which may be configured to detect touches and/or withdrawal of touches for the sensor(s) 245 may be applied to the back of each ladder rung 215 of the interactive ladder 200 and may be configured to make direct contact with the wires of the cable 245. In certain embodiments, the enclosure 240 may be 3D printed, the mount for the display device 220 may be 3D printed, and a printed circuit board may be utilized to house the electronics. The operation of the interactive ladder 200 is further explained by the method 600 described below.

Notably, as shown in FIG. 1, the system 100 may perform any of the operative functions disclosed herein by utilizing the processing capabilities of server 160, the storage capacity of the database 155, or any other component of the system 100 to perform the operative functions disclosed herein. The server 160 may include one or more processors 162 that may be configured to process any of the various functions of the system 100. The processors 162 may be software, hardware, or a combination of hardware and software. Additionally, the server 160 may also include a memory 161, which stores instructions that the processors 162 may execute to perform various operations of the system 100. For example, the server 160 may assist in processing loads handled by the various devices in the system 100, such as, but not limited to, detecting an interaction with a rung 215 of an interactive ladder 200; transmitting, from a sensor 245 that detected the interaction, a signal containing an input associated with the interaction with the rung 215 to a microcontroller 250 for processing; processing, by utilizing the microcontroller 250, the input to generate a processed input providing information associated with the interaction with the rung; providing, to a processor of a computer 260 (or other suitable device), the processed input for further processing; generating, based on the processing, an output including feedback associated with the input; causing the output including the feedback to be displayed on a display device 220 of the interactive ladder 200, wherein the output is displayed in response to the input associated with the interaction, and performing any other suitable operations conducted in the system 100 or otherwise. In one embodiment, multiple servers 160 may be utilized to process the functions of the system 100. The server 160 and other devices in the system 100, may utilize the database 155 for storing data about the devices in the system 100 or any other information that is associated with the system 100. In one embodiment, multiple databases 155 may be utilized to store data in the system 100.

The system 100 may also include a remote device 170, which may include one or more processors 172 that may be configured to process any of the various functions of the system 100. The processors 172 may be software, hardware, or a combination of hardware and software. Additionally, the remote device 170 may also include a memory 171, which stores instructions that the processors 172 may execute to perform various operations of the system 100. In certain embodiments, data from the sensors 245, the microcontroller 250, the computer 260, and/or any other component may be stored at the remote device 170, analyzed by the remote device 170, manipulated by the remote device, or a combination thereof. In certain embodiments, the remote device 170 may be configured to assist with the operations of the interactive ladder 200 itself.

Although FIGS. 1-5 illustrates specific example configurations of the various components of the system 100, the system 100 may include any configuration of the components, which may include using a greater or lesser number of the components. For example, the system 100 is illustratively shown as including a first user device 102, a second user device 111, a communications network 135, a server 140, a server 150, a server 160, a remote device 170, a database 155, an external network 165, an interactive ladder 200, a monitor 220, a cable 235, button 230, button 225, enclosure 240, stand 205, ladder rails 210, microcontroller 250, a remote controller 270 for controlling the display device 220, a circuit board 500, a cable 255, a sensor 245, and a cable 265. However, the system 100 may include multiple first user devices 102, multiple second user devices 111, multiple communications networks 135, multiple servers 140, multiple servers 150, multiple servers 160, multiple remote devices 170, multiple databases 155, multiple external networks 165, multiple interactive ladders 200, multiple monitors 220, multiple cables 235, multiple buttons 230, multiple buttons 225, multiple enclosures 240, multiple stands 205, multiple ladder rails 210, multiple microcontrollers 250, multiple remote controllers 270, multiple circuit boards 500, multiple cables 255, multiple sensors 245, multiple cables 265, and/or any number of any of the other components inside or outside the system 100. Similarly, the system 100 may include any number of data sources, applications, systems, and/or programs. Furthermore, in certain embodiments, substantial portions of the functionality and operations of the system 100 may be performed by other networks and systems that may be connected to system 100.

Figure 6:
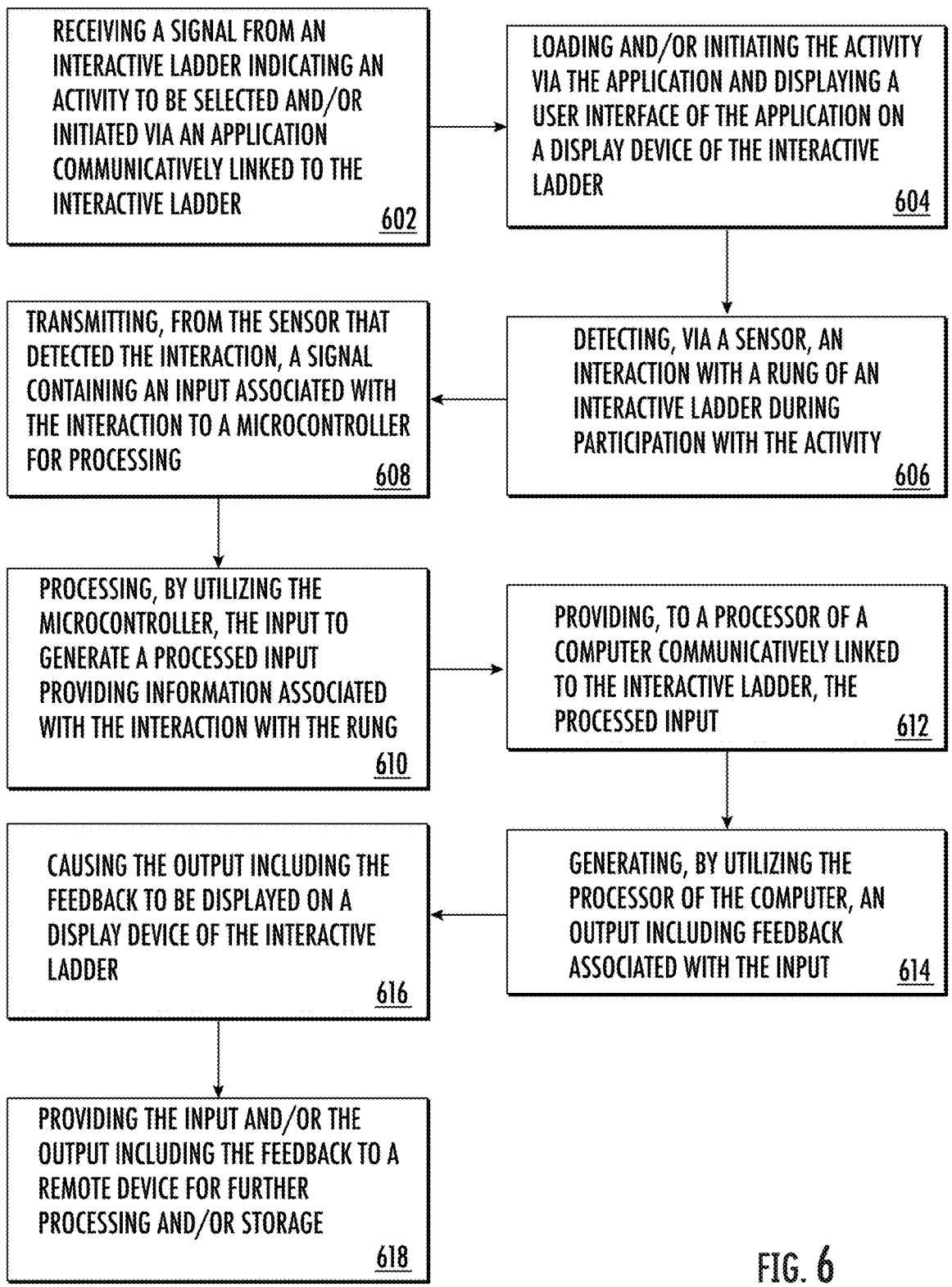
FIG. 6 is a flow diagram illustrating a sample method for utilizing an interactive ladder according to an embodiment of the present disclosure.

As shown in FIG. 6, an exemplary method 600 for utilizing an interactive ladder is schematically illustrated. The method 600 may include, at step 602, receiving a signal from an interactive ladder 200 that indicates an activity to be selected and/or initiated via an application communicatively linked to the interactive ladder 200. In certain embodiments, the receiving of the signal may be performed and/or facilitated by utilizing the first user device 102, the second user device 111, the server 140, the server 150, the server 160, the communications network 136, the external network 165, the database 155, the buttons 225, 230, the computing device 260, the microcontroller 250, any appropriate program, device, network, and/or process of the system 100, or a combination thereof. For example, the first user 101 may press or otherwise activate button 230 to select an activity displayed on a user interface of a program displayed on the display device 220. The first user 101 may utilize button 225 to exit or cancel an activity. Notably, the buttons 225, 230 may be programmed for any type of functionality. At step 604, the method 600 may include loading and/or initiating the activity via the application and presenting the activity on the user interface of the program displayed on the display device 220. For example, if the activity selected in step 602 was a game activity for matching various colored objects in the application, at step 604, the method 600 may include loading the activity and visually rendering the aspects of the program associated with the activity so that the first user 101 can participate in the activity. In certain embodiments, the loading and/or initiating of the activity may be performed and/or facilitating by utilizing the first user device 102, the second user device 111, the server 140, the server 150, the server 160, the communications network 136, the external network 165, the database 155, the buttons 225, 230, the computing device 260, the microcontroller 250, any appropriate program, device, network, and/or process of the system 100, or a combination thereof.

The first user 101 may interact with the activity (e.g. a video game, educational program, other type of program, etc.) displayed on the display device 220 by contacting one or more rungs 215 of the interactive ladder 200. For example, the first user 101 may grab a first rung 215 of the interactive ladder 200 with her left hand and a second rung 215 of the interactive ladder 200 with her right hand. Cable, such as ribbon cable 235, may be secured to each rung 215 and to the sensor 245. In certain embodiments, the interactive ladder 200 may have six rungs 215 and each rung 215 may be coupled to two wires of the ribbon cable 235. Conductive coatings (e.g. conductive ink, super shield nickel conducting coatings, and/or other types of conductive components) may be applied to each of the rungs 215 and may directly contact each of the wires on each rung 215. The other ends of the wires may be secured to input channels 237 of the sensor 245. The conductive coatings (e.g. conductive coatings 216, 217) and wires may be utilized to divide each rung 215 of the interactive ladder 200 into multiple input sections (e.g. a left side of the rung 215 and a right side of the rung 215). In certain embodiments, the conductive coatings and wires may be configured to divide each rung 215 of the interactive ladder 200 into two input sections. For example, the interactive ladder 200 may have six rungs 215, which, when divided in two, creates 12 input sections (2 in each rung) using the conductive coatings and wires of the cable 235. The conductive coatings may be utilized to detect capacitive touches (e.g. a user grabbing a rung 215, releasing her hand from the rung 215, contacting the rung 215, etc.) of the rungs 215 of the interactive ladder 200.

At step 606, the method 600 may include detecting, via the sensor 245, the wires, and the conductive coatings, the first user's 101 interaction(s) with the rungs 215 (or other parts) of the interactive ladder 200 while the first user 101 is participating in the activity. In certain embodiments, the detecting of the interaction(s) may be performed and/or facilitating by utilizing the sensor 245, the cable 235, the conductive coatings 216, 217, the first user device 102, the second user device 111, the server 140, the server 150, the server 160, the communications network 136, the external network 165, the database 155, the buttons 225, 230, the computing device 260, the microcontroller 250, any appropriate program, device, network, and/or process of the system 100, or a combination thereof. In certain embodiments, the wires of the cable 235 may be embedded in the wood frame (or other material frame) of the interactive ladder 200 and, along with the sensor 245, may relay touch and/or release data associated with the interaction(s) (e.g. a user releasing their hand from the rung 215 and/or another part of the interactive ladder 200) from the sensor 245 to the microcontroller 250 for processing. In particular, at step 608, the method 600 may include transmitting, from the sensor 245 that detected the interaction(s) (e.g. by using the sensor 245, conductive coatings 216, 217, and/or cable 235), a signal(s) containing an input (e.g. sensor data and/or other inputs) associated with the interaction to a microcontroller 250 for processing. For example, if the first user 101 grabbed the left side of the first rung 215 of the interactive ladder 200 while participating in the activity, the sensor data associated with that interaction, may be transmitted from the sensor 245 to the microcontroller 250 for further processing. As an example, grabbing the left side of the first rung 215 of the interactive ladder 200 may correspond to pairing an object displayed in the activity with another object displayed in the activity. In certain embodiments, the transmitting of the signal containing the input may be performed and/or facilitated by utilizing the sensor 245, the cable 235, the conductive coatings 216, 217, the first user device 102, the second user device 111, the server 140, the server 150, the server 160, the communications network 136, the external network 165, the database 155, the buttons 225, 230, the computing device 260, the microcontroller 250, any appropriate program, device, network, and/or process of the system 100, or a combination thereof.

At step 610, the method 600 may include processing, by utilizing the microcontroller 250, the input provided via the signal to generate a processed input. In certain embodiments, the processing may be utilized to determine additional information associated with the interaction conducted by the first user 101 with the rung 215 of the interactive ladder 200. In certain embodiments, the microcontroller 250 may determine what is happening on the interactive ladder 200 based on the input and by interpreting the sensor data. In certain embodiments, the microcontroller 250 may be configured to determine information about the sensor 245, the conductive coatings 216, 217, the wires of the cable 235, the rungs 215, the interactive ladder 200, or a combination thereof. The information may include, but is not limited to, whether a rung 215 was contacted, how the rung 215 was contacted, how long the rung 215 was contacted, how often the rung 215 is contacted, whether the run 215 was contacted using a pattern of touches, whether the first user 101 withdrew their touching of the rung 215, any interaction with the rung 215, or a combination thereof. Additionally, the information may also include, but is not limited to, what types of actions that the first user 101 has performed with respect to the interactive ladder 200, any other information, or a combination thereof. In certain embodiments, the processing of the input provided via the signal may be performed and/or facilitated by utilizing the sensor 245, the cable 235, the conductive coatings 216, 217, the first user device 102, the second user device 111, the server 140, the server 150, the server 160, the communications network 136, the external network 165, the database 155, the buttons 225, 230, the computing device 260, the microcontroller 250, any appropriate program, device, network, and/or process of the system 100, or a combination thereof.

At step 612, the method 600 may include providing the processed input to a computing device of the interactive ladder 200, such as computing device 260. In certain embodiments, the providing of the processed input to the computing device may be performed and/or facilitated by utilizing the sensor 245, the cable 235, the conductive coatings 216, 217, the first user device 102, the second user device 111, the server 140, the server 150, the server 160, the communications network 136, the external network 165, the database 155, the buttons 225, 230, the computing device 260, the microcontroller 250, any appropriate program, device, network, and/or process of the system 100, or a combination thereof. The computing device 260 may serve as the central computing unit that connects to all of the other components of the interactive ladder 200 and/or the system 100 in general. The computing device 260 may run the software program/application that the first user 101 is interacting with via the interactive ladder 200. The computing device 260 may provide some or all of the functionality of the application and may facilitate rendering of the graphical user interface of the application on the display device 220. In certain embodiments, the application may present game-like versions of physical therapy activities and challenges. The first user 101, for example, can choose from a menu of activities to participate in using the application, and each activity can have its own instructions, objectives, and themes so as to create an enjoyable and interactive therapy session. In certain embodiments, the computing device 260 can record any incoming data and/or inputs, and may be configured to analyze and visualize the first user's 101 performance and/or interactions over time as they relate to the first user's 101 participation in each activity.

At step 614, the method 600 may include generating, by utilizing the computing device 260, an output based on the input received from the microcontroller 250. In certain embodiments, the output may include feedback and information about the first user's 101 actions with respect to the interactive ladder 200 and the application that the first user 101 is interacting with. In certain embodiments, the output may include context information associated with the interactions and specific aspects of the feedback. For example, in the color matching example, the computing device 260 may determine that the interaction that the first user 101 conducted with the first rung 215 of the interactive ladder 200 indicates that the first user 101 correctly color-matched two objects being displayed on the display device 220. In certain embodiments, the output may include text feedback, visual feedback, haptic feedback, a confirmation of a correct action, audio feedback, any type of feedback, information describing the input, information indicating a next action to perform, information indicating an adjustment to make to the application and/or to a function of the application, any type of output, or a combination thereof. In certain embodiments, the generating of the output may be may be performed and/or facilitated by utilizing the sensor 245, the cable 235, the conductive coatings 216, 217, the first user device 102, the second user device 111, the server 140, the server 150, the server 160, the communications network 136, the external network 165, the database 155, the buttons 225, 230, the computing device 260, the microcontroller 250, any appropriate program, device, network, and/or process of the system 100, or a combination thereof.

At step 616, the method 600 may include causing the output including the feedback to be displayed, presented, and/or otherwise outputted on the display device 220 and/or other components of the interactive ladder 200. In certain embodiments, the output may be visual content, audio content, haptic feedback, any type of output, or a combination thereof. In certain embodiments, the output may involve causing the application to progress to a new screen, manipulate a digital character, perform various actions in the application, perform any type of computer/application operation, or any combination thereof. In certain embodiments, the output may be outputted via speakers, haptic components, vibration components, media components, and/or any output interface of the interactive ladder 200. In certain embodiments, displaying, presenting, and/or outputting of the output including the feedback may be performed and/or facilitated by utilizing the sensor 245, the cable 235, the conductive coatings 216, 217, the first user device 102, the second user device 111, the server 140, the server 150, the server 160, the communications network 136, the external network 165, the database 155, the buttons 225, 230, the computing device 260, the microcontroller 250, any appropriate program, device, network, and/or process of the system 100, or a combination thereof.

At step 618, the method 600 may include providing the input and/or output including the feedback to a remote device for further processing, analysis, and/or storage. For example, the providing may encompass transmitting the input and/or output including the feedback to servers 140, 150 160, computing device 170, second user device 111, external network 165, first user device 102, database 155, any other component, device, and/or program of system 100, or any combination thereof. In certain embodiments, the providing of the input and/or output including the feedback may be performed and/or facilitated by utilizing the sensor 245, the cable 235, the conductive coatings 216, 217, the first user device 102, the second user device 111, the server 140, the server 150, the server 160, the communications network 136, the external network 165, the database 155, the buttons 225, 230, the computing device 260, the microcontroller 250, any appropriate program, device, network, and/or process of the system 100, or a combination thereof. In certain embodiments, once the input and/or output including the feedback are provided to the remote device, the remote device may perform further analyses on the input and/or output. For example, the remote device can determine patterns of interaction with the interactive ladder 200, if the first user 101 is improving performance during activities over time, if the first user 101 is having any difficulties performing the activities, what types of activities are assisting the first user 101 in learning and/or developing motor skills, and/or any combination thereof. In certain embodiments, the analyses conducted by the remote device may be utilized to determine the optimal activities for a particular user, such as the first user 101. Notably, the method 600 may further incorporate any of the features and functionality described for the system 100 or as otherwise described herein.

The systems and methods disclosed herein may include additional functionality and features. For example, the operative functions of the system 100 and method may be configured to execute on a special-purpose processor specifically configured to carry out the operations provided by the system 100 and method. Notably, the operative features and functionality provided by the system 100 and method may increase the efficiency of computing devices that are being utilized to facilitate the functionality provided by the system 100 and method 600. For example, through the use of the devices, components, programs, and/or networks of the system 100, machine learning and/or artificial intelligence capabilities may be utilized so as to reduce the amount of computer operations need to be performed by the devices in the system 100 using the processors and memories of the system 100 than in systems that are not capable of machine learning as described in this disclosure. In such a context, less processing power needs to be utilized because the processors and memories do not need perform analyses and operations that have already been learned by the system 100. As a result, there may be substantial savings in the usage of computer resources by utilizing the software, functionality, and algorithms provided in the present disclosure.

Notably, in certain embodiments, various functions and features of the system 100 and methods may operate without human intervention and may be conducted entirely by computing devices, robots, and/or processes. For example, in certain embodiments, multiple computing devices may interact with the interactive ladder 200 of the system 100 to provide the functionality supported by the system 100. Additionally, in certain embodiments, the computing devices of the system 100 may operate continuously to reduce the possibility of errors being introduced into the system 100. In certain embodiments, the system 100 and methods may also provide effective computing resource management by utilizing the features and functions described in the present disclosure. For example, in certain embodiments, when analyzing sensor data and/or inputs obtained via sensors 245 of the system 100, any selected device in the system 100 may transmit a signal to a computing device (e.g. computing device 260) receiving or processing the input that only a specific quantity of computer processor resources (e.g. processor clock cycles, processor speed, processor cache, etc.) may be dedicated to processing the sensor data to generate outputs and/or feedback, performing any other operation conducted by the system 100, or any combination thereof. For example, the signal may indicate an amount of processor cycles of a processor that may be utilized to process the sensor data, and/or specify a selected amount of processing power that may be dedicated to processing the sensor data or any of the other operations performed by the system 100. In certain embodiments, a signal indicating the specific amount of computer processor resources or computer memory resources to be utilized for performing an operation of the system 100 may be transmitted from the interactive ladder 200, the computing device 260, the microcontroller 250, the sensor 245, and/or the first and/or second user devices 102, 111 to the various components and devices of the system 100.

In certain embodiments, any device in the system 100 may transmit a signal to a memory device to cause the memory device to only dedicate a selected amount of memory resources to the various operations of the system 100. In certain embodiments, the system 100 and methods may also include transmitting signals to processors and memories to only perform the operative functions of the system 100 and methods at time periods when usage of processing resources and/or memory resources in the system 100 is at a selected, predetermined, and/or threshold value. In certain embodiments, the system 100 and methods may include transmitting signals to the memory devices utilized in the system 100, which indicate which specific portions (e.g. memory sectors, etc.) of the memory should be utilized to store any of the data utilized or generated by the system 100. Notably, the signals transmitted to the processors and memories may be utilized to optimize the usage of computing resources while executing the operations conducted by the system 100. As a result, such features provide substantial operational efficiencies and improvements over existing technologies.

Figure 7:
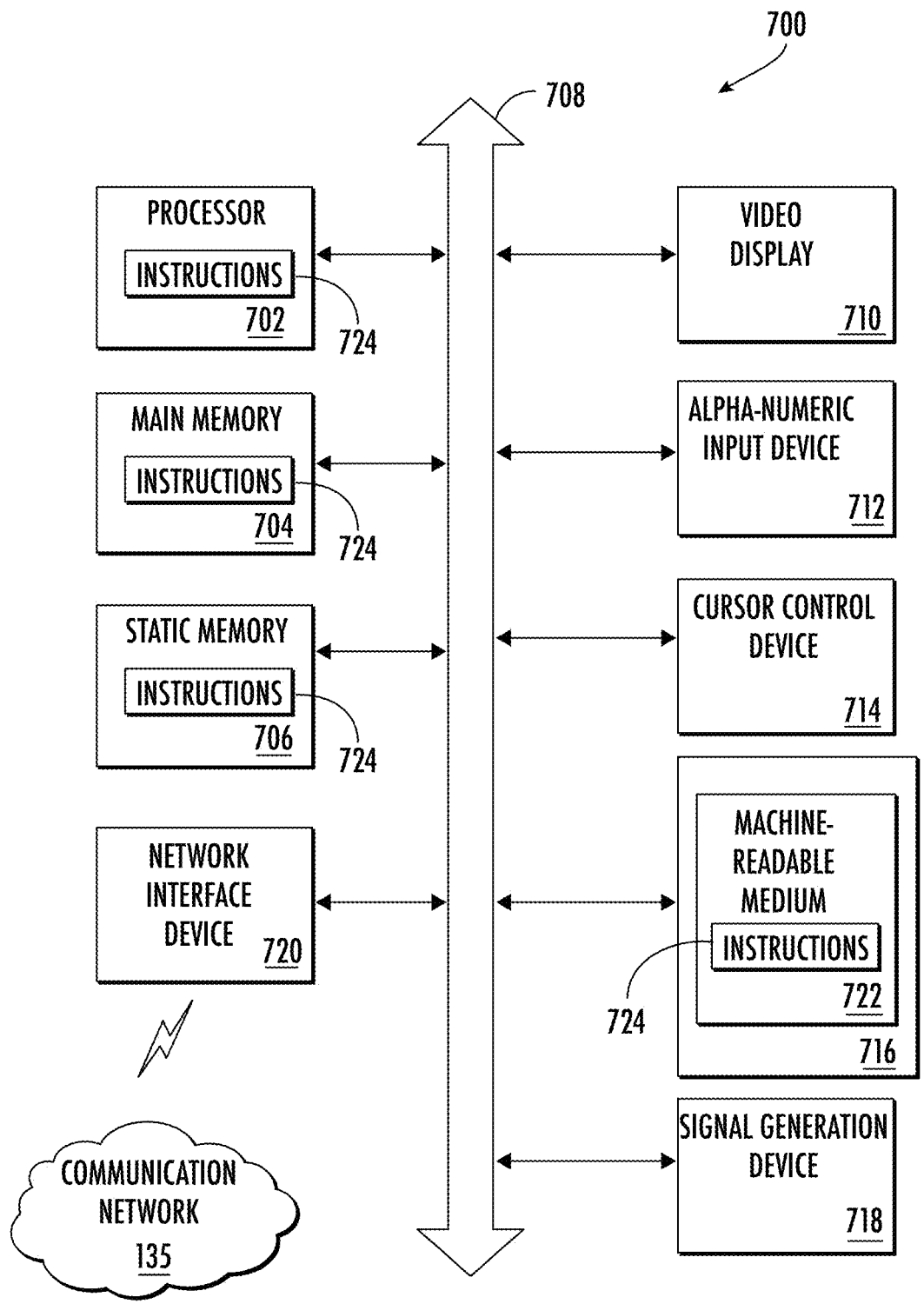
FIG. 7 is a schematic diagram of a machine in the form of a computer system within which a set of instructions, when executed, may cause the machine to perform any one or more of the methodologies or operations of the systems and methods for utilizing an interactive ladder.

Referring now also to FIG. 7, at least a portion of the methodologies and techniques described with respect to the exemplary embodiments of the system 100 can incorporate a machine, such as, but not limited to, computer system 700, or other computing device within which a set of instructions, when executed, may cause the machine to perform any one or more of the methodologies or functions discussed above. The machine may be configured to facilitate various operations conducted by the system 100. For example, the machine may be configured to, but is not limited to, assist the system 100 by providing processing power to assist with processing loads experienced in the system 100, by providing storage capacity for storing instructions or data traversing the system 100, or by assisting with any other operations conducted by or within the system 100.

In some embodiments, the machine may operate as a standalone device. In some embodiments, the machine may be connected (e.g., using communications network 135, the external network 165, another network, or a combination thereof) to and assist with operations performed by other machines, programs, functions, and systems, such as, but not limited to, the first user device 102, the second user device 111, the server 140, the server 150, the database 155, the server 160, the external network 165, the computing device 170, the interactive ladder 200, the sensor 245, the computing device 260, the microcontroller 250, the display device 220, the communications network 135, any device, system, and/or program in FIGS. 1-7, or any combination thereof. The machine may be connected with any component in the system 100. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 700 may include a processor 702 (e.g., a central processing unit (CPU), a graphics processing unit (GPU, or both), a main memory 704 and a static memory 706, which communicate with each other via a bus 708. The computer system 700 may further include a video display unit 710, which may be, but is not limited to, a liquid crystal display (LCD), a flat panel, a solid state display, or a cathode ray tube (CRT). The computer system 1100 may include an input device 712, such as, but not limited to, a keyboard, a cursor control device 714, such as, but not limited to, a mouse, a disk drive unit 716, a signal generation device 718, such as, but not limited to, a speaker or remote control, and a network interface device 720.

The disk drive unit 716 may include a machine-readable medium 722 on which is stored one or more sets of instructions 724, such as, but not limited to, software embodying any one or more of the methodologies or functions described herein, including those methods illustrated above. The instructions 724 may also reside, completely or at least partially, within the main memory 704, the static memory 706, or within the processor 702, or a combination thereof, during execution thereof by the computer system 700. The main memory 704 and the processor 702 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine-readable medium 722 containing instructions 724 so that a device connected to the communications network 135, the external network 165, another network, or a combination thereof, can send or receive voice, video or data, and communicate over the communications network 135, the external network 165, another network, or a combination thereof, using the instructions. The instructions 724 may further be transmitted or received over the communications network 135, the external network 165, another network, or a combination thereof, via the network interface device 720.

While the machine-readable medium 722 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other rewritable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of apparatus and systems that might make use of the structures described herein. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

We claim:

1. An interactive ladder, comprising:
a display device;
a rung, wherein the display device is positioned behind the rung of the interactive ladder;
a sensor configured to detect an interaction with the rung;
a microcontroller configured to receive a signal containing an input associated with the interaction from the sensor, and, wherein the signal containing the input is provided by the sensor in response to the interaction with the rung being detected; and
a computer including a processor configured to perform operations, the operations comprising:
receiving the signal containing the input from the microcontroller, wherein the input provides information associated with the interaction with the rung;
processing the input to generate an output including feedback associated with the input; and
causing the output including the feedback to be displayed on the display device in response to the input associated with the interaction.

2. The interactive ladder of claim 1, wherein the operation of processing the input to generate the output including the feedback includes generating visual feedback, auditory feedback, haptic feedback, virtual reality feedback, augmented reality feedback, any type of feedback, or a combination thereof.

3. The interactive ladder of claim 1, wherein the operation of causing the output including the feedback to be displayed includes causing the output to be displayed on a user interface of an application that a user of the interactive ladder is interacting with.

4. The interactive ladder of claim 1, further comprising a first button, which when pressed, selects an activity to be performed via an application communicatively linked to the interactive ladder, and further comprising a second button, which when pressed, facilitates an exit from the activity, a return to a digital menu of the application, control the application, or a combination thereof.

5. The interactive ladder of claim 1, further comprising a ribbon cable coupled to the rung, wherein the ribbon cable is configured to be coupled to the sensor, the microcontroller, or a combination thereof.

6. The interactive ladder of claim 5, further comprising a conductive component applied to the rung and configured to make direct contact with the ribbon cable.

7. The interactive ladder of claim 6, wherein the rung, upon being interacted with, causes the signal containing the input associated with the interaction to be transmitted via the conductive component and the ribbon cable to the sensor.

8. The interactive ladder of claim 1, further comprising an enclosure for housing the microcontroller and the sensor.

9. The interactive ladder of claim 1, further comprising a mount configured to attach to the display device and to a ladder base of the interactive ladder.

10. The interactive ladder of claim 1, wherein the operations further comprise navigating between options provided in a digital menu displayed on a user interface of an application displayed on the display device based on the input.

11. The interactive ladder of claim 1, wherein the operations further comprise displaying a user interface of a gaming application, a user interface of an educational application, a user interface of a therapy application, a user interface of a productivity application, a user interface of any application, or a combination thereof, on the display device.

12. The interactive ladder of claim 1, wherein the rung comprises a plurality of rungs and the sensor comprises a plurality of channels.

13. The interactive ladder of claim 1, wherein each rung of the plurality of rungs is connected to at least two channels of the plurality of channels of the sensor via conductive components and ribbon cables positioned on each rung.

14. A method, comprising:
detecting an interaction with a rung of an interactive ladder;
transmitting, from a sensor that detected the interaction, a signal containing an input associated with the interaction with the rung to a microcontroller for processing;
processing, by utilizing the microcontroller, the input to generate a processed input providing information associated with the interaction with the rung;
providing, to a processor, the processed input for further processing;

generating, based on the processing, an output including feedback associated with the input; and causing the output including the feedback to be displayed on a display device of the interactive ladder that is positioned behind the rung of the interactive ladder, wherein the output is displayed in response to the input associated with the interaction.

15. The method of claim 14, further comprising detecting the interaction with the rung via a conductive component and a ribbon cable coupled to the rung of the interactive ladder, wherein the conductive component is configured to detect a touch performed by a user on the rung and a withdrawal of the touch on the rung by the user.

16. The method of claim 14, further comprising transmitting the output to a mobile device, a network, any device, or a combination thereof.

17. The method of claim 14, further comprising utilizing the output to adjust functionality of an application being interacted with via the interactive ladder.

18. The method of claim 14, further comprising receiving a signal from a button of the interactive ladder, wherein the signal indicates an activity to be selected from an application communicatively linked to the interactive ladder, an indication to exit from the activity, an indication to navigate through a digital menu of the application, an indication to control the application, an indication to perform an operation in the application, any indication, or a combination thereof.

19. The method of claim 14, further comprising activating a speaker based on the input, activating a light based on the input, activating a haptic component based on the input, or a combination thereof.

20. A system, comprising:

an interactive ladder comprising a rung;

a sensor configured to detect an interaction with the rung;

a microcontroller configured to receive a signal containing an input associated with the interaction from the sensor, and, wherein the signal containing the input is provided by the sensor in response to the interaction with the rung being detected; and a computer including a processor configured to perform operations, the operations comprising receiving the signal containing the input from the microcontroller, wherein the input provides information associated with the interaction with the rung;

processing the input to generate an output including feedback associated with the input; and causing the output including the feedback to be displayed on a display device located behind the rung in response to the input associated with the interaction.

* * * * *